United States Patent [19]

Avidan et al.

[11] Patent Number: 4,778,661
[45] Date of Patent: Oct. 18, 1988

[54] UPGRADING DIENE-CONTAINING LIGHT OLEFINS IN A FLUIDIZED BED REACTOR

[75] Inventors: Amos A. Avidan, Mantua, N.J.; Fritz A. Smith, New Hope, Pa.; Samuel A. Tabak, Wenonah, N.J.

[73] Assignee: Mobil Oil Corporation, New York, N.Y.

[21] Appl. No.: 6,408

[22] Filed: Jan. 23, 1987

[51] Int. Cl.$^4$ .............................................. B01J 8/24
[52] U.S. Cl. ...................... 422/146; 422/143; 422/207; 422/140
[58] Field of Search ............... 422/139, 140, 143, 144, 422/146, 207; 208/157; 34/10 A

[56] References Cited

U.S. PATENT DOCUMENTS

| | | | |
|---|---|---|---|
| 2,863,823 | 12/1958 | Moser, Jr. | 208/157 |
| 3,071,540 | 1/1963 | McMahon et al. | 208/157 |
| 3,843,740 | 10/1974 | Mitchell et al. | |
| 4,052,477 | 10/1977 | Ireland et al. | |
| 4,070,411 | 1/1978 | Butter et al. | |
| 4,097,367 | 6/1978 | Haag et al. | |
| 4,100,218 | 7/1978 | Chen et al. | |
| 4,251,484 | 2/1981 | Davidak et al. | 422/140 |
| 4,254,295 | 3/1981 | Tabak | |
| 4,417,086 | 11/1983 | Miller | |
| 4,417,087 | 11/1983 | Miller | |
| 4,434,049 | 2/1984 | Dean et al. | 208/157 |
| 4,517,396 | 5/1985 | Hoek et al. | |
| 4,547,616 | 10/1985 | Avidan et al. | |
| 4,555,328 | 11/1985 | Krambeck et al. | 422/140 |
| 4,562,046 | 12/1985 | Hays et al. | 208/157 |
| 4,605,807 | 8/1986 | Mazurek | |

FOREIGN PATENT DOCUMENTS 2156381 10/1985 United Kingdom .

Primary Examiner—Michael S. Marcus
Attorney, Agent, or Firm—Alexander J. McKillop; Michael G. Gilman; L. G. Wise

[57] ABSTRACT

An improved fluidized bed process for upgrading olefinic hydrocarbon feedstock by contacting the feedstock with acidic siliceous zeolite conversion catalyst particles at elevated temperature under exothermic conditions to produce heavier hydrocarbons including gasoline range hydrocarbons. The improvement comprises maintaining a turbulent fluidized bed of catalyst particles by flowing hydrocarbon-containing vapor upwardly through said bed at less than transport velocity; and introducing liquid olefinic feedstock comprising at least one $C_4$–$C_6$ diene component into the fluidized catalyst bed in a lower portion thereof by rapidly atomizing and vaporizing the liquid feedstock, thus converting feedstock to heavier hydrocarbon without substantial thermal diene degradation thereof prior to contacting conversion catalyst particles in the fluidized bed. Reaction severity conditions may be maintained by controlling catalyst acidity, reaction temperature and reactant contact time to produce reaction effluent containing propane and propene in the ratio of about 0.2:1 to 200:1. A predominantly liquid product is recovered containing $C_4$–$C_9$ hydrocarbons rich in olefins and aromatics.

3 Claims, 2 Drawing Sheets

UPGRADING DIENE-CONTAINING LIGHT OLEFINS IN A FLUIDIZED BED REACTOR

BACKGROUND OF THE INVENTION

This invention relates to a catalytic technique for upgrading olefin streams rich in dienes to heavier hydrocarbons rich in aliphatics and aromatics. In particular, it provides a continuous process for oligomerizing a feedstock containing monoalkenes and dienes to produce $C_5+$ hydrocarbons, such as liquid fuels, isobutane, aromatics and other useful products. Diene-containing liquids, such as thermal cracking liquids, are useful feedstock herein.

Developments in zeolite catalysis and hydrocarbon conversion processes have created interest in utilizing olefinic feedstocks for producing $C_5+$ gasoline, diesel fuel, etc. In addition to basic chemical reactions promoted by ZSM-5 type zeolite catalysts, a number of discoveries have contributed to the development of new industrial process. These are safe, enironmentally acceptable processes for utilizing feedstocks that contain olefins. Conversion of $C_2-C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zoelites having controlled acidity. Garwood et al. have also contributed to the understanding of catalytic olefin uprgrading techniques and improved processes as in U.S. Pat. Nos. 4,150,062, 4,211,640 and 4,227,992. The above-identified disclosures are incorporated herein by reference.

Conversion of olefins, especially propene and butenes, over HZSM-5 is effective at moderately elevated temperatures and pressures. The conversion products are sought as liquid fuels, especially the $C_5+$ aliphatic and aromatic hydrocarbons and $C_4$ hydrocarbons, in particular iso-butane. Product distribution for liquid hydrocarbons can be varied by controlling process conditions, such as temperature, pressure and space velocity. Gasoline ($C_5-C_{10}$) is readily formed at elevated temperature [(e.g., up to about 700° C.)] and moderate pressure from ambient to about 5500 kPa, preferably about 200 to 2900 kPa. Olefinic gasoline can be produced in good yield and may be recovered as a product or fed to a low severity, high pressure reactor system for further conversion to heavier distillate-range products. Distillate mode operation can be employed to maximize production of $C_{10}+$ aliphatics by reacting the lower and intermediate olefins at high pressure and moderate temperature. Operating details for typical "MOGD" oligomerization units are dislcosed in U.S. Pat. Nos. 4,456,779; 4,497,968 (Owen et al.) and 4,433,185 (Tabak), incorporated herein by reference. At moderate temperature and relatively high pressure, the conversion conditions favor distillate-range product having a normal boiling point of at least 165° C. (330° F.).

Many feedstocks of commercial interest, such as thermal cracking byproduct, etc., contain both mono-olefins and diolefins (e.g. $C_2-C_6$ mono-alkenes and $C_4+$ dienes) along with $C_1-C_{10}$ light aliphatics, and a minor amount of aromatics. Gaseous and liquid streams containing dienes are typically produced in thermal cracking operations. One common example is pyrolysis gasoline, which is produced as ethene (ethylene) byproduct. Such diene-containing streams are often difficult to process due to poor thermal stability and the tendency of dienes to form coke and gum deposits. This complicates preheating of such streams into the high temperatures required of most catalytic upgrading processes. Prior attempts to upgrade such materials have pretreated the feedstock to hydrogenate the diolefin selectively, as in U.S. Pat. No. 4,052,477 (Ireland et al). The present invention is concerned with providing a safe and low cost technique for catalytically converting diene-rich streams to high value $C_4+$ products rich in aromatics.

It has been found that diene-containing olefinic light hydrocarbons can be uprgraded directly to liquid hydrocarbons rich in $C_5+$ aliphatics and aromatics by catalytic conversion in a turbulent fluidized bed of solid acid zeolite catalyst under high severity reaction conditions without deleterious effects from the diolefin components. This technique is particularly useful for upgrading $C_4+$ liquid pyrolysis products, which may contain minor amounts ethene, propene, $C_2-C_4$ paraffins and hydrogen produced in cracking petroleum fractions, such as naphtha, ethane or the like. By upgrading the complex olefinic by-product, gasoline yield of cracking units can be significantly increased. Accordingly, it is a primary object of the present invention to provide a novel technique for upgrading diene-rich hydrocarbon steams.

SUMMARY OF THE INVENTION

A process has been found for continuous conversion of diene-containing olefinic feedstock to heavier hydrocarbon products wherein the feedstock is contacted at elevated temperature with a fluidized bed of acidic siliceous zeolite catalyst under high severity conversion conditions. The improvement herein comprises the steps of maintaining a turbulent fluidized bed of catalyst particles by flowing hydrocarbon-containing vapor upwardly through the bed at less than transport velocity and by introducing liquid olefinic feedstock comprising at least one $C_4-C_6$ diene component into the fluidized catalyst bed in a lower bed portion by rapdily atomizing and vaporizing the liquid feedstock, thus converting feedstock to heavier hydrocarbon without substantial thermal diene degradation thereof prior to contacting conversion catalyst particles in the fluidized bed. This technique prevents fouling of conduits, furnaces and other upstream equipment.

In a preferred embodiment of the invention, the olefinic feed comprises about 5 to 90 wt. % total $C_4+$ mono-olefin and 5 to 50 wt. % conjugated unsaturated dienes, and the fluidized bed is maintained at an average temperature of about 315° to 510° C. The preferred catalyst comprises medium pore shape selective metallosilicate.

In a turbulent fluidized catalyst bed the conversion reactions are conducted in a vertical reactor column by passing feedstock gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity whereby propane:propene molar ratio in the hydrocarbon product is maintained at about 0.2:1 to 200:1 under conditions of reaction severity to effect feedstock conversion. A thermodynamically balanced mixture of exothermic alkenes and endothermic alkanes can be converted without significant recycle and/or diluent. However, a supplemental feedstream or recycle stream such as $C_3^-$ hydrocarbons can be introduced into the reactor bed. Such a recycle stream can increase $C_5^+$ aliphatic and aromatic yields, while lowering catalyst makeup requirements.

DESCRIPTION OF PREFERRED EMBODIMENTS

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B, Fe or mixtures thereof, within the zoelitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e, about 5–7A) shape-selective crystalline aluminosilicate zeolites having a silica-to-alumina ratio of at least 12, a constraint index of about 1 to 12 and acid cracking activity (alpha value) of about 10–250, preferably about 10 to 80 based on total catalyst weight. In the fluidized bed reactor the coked catalyst may have an apparent activity (alpha value) of about 10 tp 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, ZSM-38, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,106,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and aromatization characteristics. A typical zeolite catalyst component having Bronsted acid sites may consist essentially of aluminosilicate ZSM-5 zeolite with 5 to 95 wt.% silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particular. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt %, of the monoalkenes and dienes in the feestock. In the description of preferred embodiments a 25% H-ZSM-5 catalyst calcined with 75% silica-alumina matrix binder is employed unless otherise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This size range of fluidizable particles is classified as Geldart Group A. The fluidization regime is controlled to assure operation between the transition velocity and transport velocity, and these fluidization conditions are substantially different from those found in non-turbulent dense beds or transport beds.

Process Operation

In this description, metric units and parts by weight are employed unless otherwise stated.

Suitable olefinic feedstocks comprises $C_4$–$C_6$ alkenes including conjugated dienes such as 1,3-butadiene, pentadiene isomers, hexadienes, cyclic dienes, or similar $C_4^+$ aliphatic liquid hydrocarbons having diethylenic conjugated unsaturation. Aromatics coproduced with the liquid olefinic components may be cofed or separated by solvent extraction prior to conversion of the diene-rich feedstock. Non-deleterious components, such as paraffins and inert gases, may be present. A particularly useful feedstock is a liquid by-product of pyrolysis or thermal cracking units containing typically 40–95 wt % $C_4$–$C_6$ total mono-olefins and di-olefins, including about 5–60 wt. % diene, along with varying amounts of $C_3$–$C_8$ paraffins, aromatics and inerts. Specific examples are given in Table 1 below. The process may be tolerant of a wide range of lower alkanes, from 0 to 95%. Preferred pyrolysis feedstocks contain more than 50 wt. % $C_4$–$C_6$ lower aliphatic hydrocarbons, and contain sufficient olefins to provide an olefinic partial pressure of at least 50 kPa. Under the high severity reaction conditions employed in the present invention, lower alkanes may be partially converted to heavier hydrocarbonds The desired products are $C_5$ to $C_9$ hydrocarbons, which will ordinarily comprise at least 50% of the recovered product, peferrable 80% or more. While olefins may be a predominant fraction of the $C_5^+$ reaction effluent; it is often desired to upgrade the feedstock to high octane gasoline containing aromatics, preferrably at least 5% $C_6$–$C_8$ aromatics (BTX).

The reaction severity conditions can be controlled to optimize yield of $C_4$–$C_9$ hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 100 to significantly lower values under steady state operation by controlling catalyst deactivation and regeneration rates to provide an apparent average alpha value below 100, preferably about 15 to 80.

Reaction temperatures and contact time are also significant factors in the reaction severity, and the process parameters are followed to give a substantially steady state condition wherein the reaction severity index (R.I.) is maintained within the limits which yield a desired weight ratio of propane to propene. While this index may vary from about 0.2 to 200, it is preferred to operate the steady state fluidized bed unit to hold the R.I. below about 50, with optimum operation at 0.7 to 2 in the substantial absence of added propane. While reaction severity is advantageously determined by the weight ratio of propane:propene in the gasoues phase, it may also be approximated by the analogous ratios of butanes:butenes, pentanes:pentenes, or the average of total reactor effluent alkanes:alkenes in the $C_3$–$C_5$ range. Accordingly, these alternative expressions may be a more accurate measure of reaction severity conditions when propane is added to the feedstock. The optimal value will depend upon the exact catalyst composition, feedstock and reaction conditions; however, the typical diene-rich feed mixtures used in the examples herein and additional olefinic feeds can be optimally upgraded to the desired aliphatic-rich gasoline by keeping the R.I. at about 1.

Upgrading of olefins by such hydrogen contributors in fluidized bed cracking and oligomerization units is taught by Owen et al in U.S. Pat. No. 4,090,949. This technique is particularly useful for operation with a pyrolysis cracking unit to increase overall production of liquid product.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances, often less than 5° C. Except for a small zone adjacent the bottom gas inlet, the midpoint measurement is representative of the entire bed, due to the thorough mixing achieved.

Figure 1:
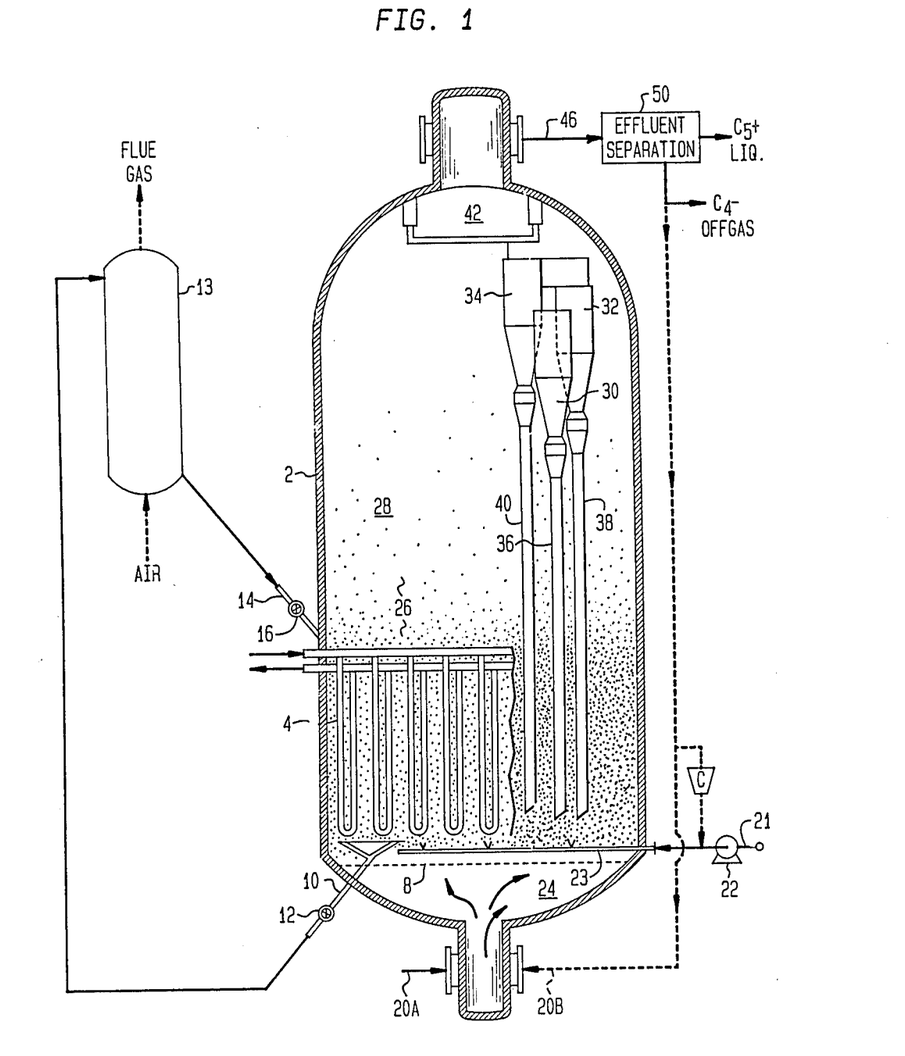
FIG. 1 is a schematic view of a fluidized bed reactor system according to the present invention.

Referring now to FIG. 1, a reactor vessel 2 is shown provided with heat exchange tube means 4. There may be several separate heat exchange steam generating tube bundles so that temperature control can be separately exercised over the fluid catalyst bed. The bottoms of the tubes are spaced above a feed distributor grid 8 sufficiently to be free of jet action by the charged gas passing through the small diameter holes in the grid 8. Although depicted without baffles, the vertical reaction zone can contain open end tubes above the grid for maintaining hydraulic constraints, as disclosed in U.S. Pat. No. 4,251,484 (Daviduk and Haddad). Optionally, a variety of horizontal baffles may be added to limit axial mixing in the reactor. Heat released from the reaction can be controlled by adjusting feed temperature in a known manner. A large portion of reaction heat can be removed by feeding cold liquid into the reactor at a temperature at least 200° C. below average bed temperature. In the reactor configuration shown the heat exchanger tubes can function as dummy tubes to limit mixing in the reactor.

The system provides for withdrawing catalyst from above grid 8 by conduit means 10. This flow line can be provided with control valve means 12 for passage to catalyst regeneration in vessel 13, where coked catalyst particles are oxidatively regenerated in contact with air or other regeneration gas at high temperature. The oxidatively regenerated catalyst is then passed to the reactor fluid bed of catalyst by conduit means 14 and flow control valve 16. The regenerated catalyst is charged to the catalyst bed sufficiently below the upper interface to achieve good mixing in the fluid bed. Since the flow of regenerated catalyst passed to the reactor can be relatively small, hot regenerated catalyst does not ordinarily upset the temperature constraints of the reactor operations in a significant amount.

Initial fluidization is achieved by forcing a lift gas upwardly through the catalyst, a light aliphatic $C_4^-$ gas, with or without diluent or recycle, may be charged through inlet port 20A at a bottom portion of the reactor in open communication with chamber 24 beneath grid 8. Pressurized feedstock is introduced above reactant distributor grid 8 via supply conduit 21, pump 22 and distributor conduit 23 to one or more spray nozzle means, described and depicted in FIG. 2. The liquid is dispersed into the bed of the catalyst thereabove at a velocity sufficient to form a generally upwardly flowing suspension of atomized liquid reactant with the catalyst particles and lift gas.

Advantageously, the liquid diene-containing reactant feed is injected into the catalyst bed by atomizing the pressurized liquid feedstream to form readily dispersible liquid particles having an average size of 300 microns or less. This contributes to rapid vaporization of the liquid at process pressure. Exothermic conversion provides sufficient heat to vaporize the liquid quickly, thus avoiding deleterious liquid phase reactions of the diene components, which tend to form carbonaceous deposits such as heavy coke, gums, etc.

A plurality of sequentially connected cyclone separator means 30, 32 and 34 provided with diplegs 36, 38 and 40 respectively are positioned in an upper portion of the reactor vessel comprising dispersed catalyst phase 28.

The product effluent separated from catalyst particles in the cyclone separating system then passes to a plenum chamber 42 before withdrawal via conduit 46, operatively connect with effluent separation system 50. The product effluent is cooled and separated to recover $C_5+$ liquid hydrocarbons, gaseous recycle or offgas, along with any byproduct water or catalyst fines carried over. A portion of the light gas effluent fraction may be recycled by compressing to form a motive gas for the liquid feed or via recycle conduit 20B for use as lift gas. The recovered hydrocarbon product comprising $C_5+$ olefins and/or aromatics, paraffins and naphthenes is thereafter processed as required to provide a desired gasoline or higher boiling product.

Under optimized process conditions the turbulent bed has a superficial vapor velocity of about 0.3 to 2 meters per second (m/sec). At higher velocities entrainment of fine particles may become excessive and beyond 10 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 kg/m$^3$, preferrably about 300 to 500, measured at the bottom of the reaction zone, becoming less dense toward the top of the reaction zone due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having a clean apparent density of 1.06 gm/cc and packed density of 0.85, an average fluidized bed density of about 300 to 500 kg/m$^3$ is satisfactory.

By virtue of the turbulence experienced in the turbulent regime, gas-solid contact in the catalytic reactor is improved, providing substantially complete conversion, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A significant difference between the process of this invention and conversion processes of the prior art is that operation in the turbulent fluidization regime is optimized to produce high octane $C_5+$ liquid in good yield. The weight hourly space velocity and uniform contact provides a close control of contact time between vapor and solid phases, typically about 3 to 25 seconds. Another advantage of operating in such a mode is the control of bubble size and life span, thus avoiding large scale gas by-passing in the reactor. The process of the present invention does not rely on internal baffles in the reactor for the purpose of bubble size control such as the baffles which are employed in the prior art dense bed processes discussed above.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity, as described by Avidan et al in U.S. Pat. No. 4,547,616 and by Tabak et al. in U.S. Pat. No. 4,579,999, incorporated herein by reference. As the transport velocity is approached, there is a sharp increase in the rate of particle carryover, and in the absence of solid recycle, the bed could empty quickly.

Several useful parameters contribute to fluidization in the turbulent regime in accordance with the process of the present invention. When employing a ZSM-5 type zeolite caytalyst in fine powder form such a catalyst should comprise the zeolite suitably bound or impregnated on a suitable support with a solid density (weight of a representative individual particle divided by its apparent "outside" volume) in the range from 0.6–2 g/cc, preferably 0.9–1.6 g/cc. The catalyst particles can be in a wide range of particle sizes up to about 250 microns, with an average particle size between about 20 and 100 microns, preferably in the range of 10–150 microns and with the average particle size between 40 and 80 microns. When these solid particles are placed in a fluidized bed where the superficial fluid velocity is 0.3–2, operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5–20 meters in height, preferably about 7 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone disposed within the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with any process stream which contains sufficient liquid olefins and dienes and is substantially free of deleterious oxygenates and sulfur compounds. Experimental runs are performed using a ZSM-5 catalyst to demonstrate the inventive process. The fluidized bed unit can be operated over a wide range of process variables and catalyst activity.

Reactor Operation

A typical single pass reactor unit employs a temperature-controlled catalyst zone with indirect heat exchange and/or adjustable gas quench, whereby the reaction exotherm can be carefully controlled to prevent excessive temperature above the usual operating range of about 315° C. to 510° C., preferably at average reactor temperature of 340° C. to 430° C. Energy conservation in the system may utilize at least a portion of the reactor exotherm heat value by exchanging hot reactor effluent with feedstock and/or recycle streams. Optional heat exchangers may recover heat from the effluent stream prior to fractionation. It is preferred to operate the olefin conversion reactors at moderate pressure of about 100 to 3000 kPa (atmostpheric to about 400 psig).

The weight hourly space velocity (WHSV, based on total olefins in the fresh feedstock is about 0.1–5 WHSV. Typical product fractionation systems are described in U.S. Pat. Nos. 4,456,779 and 4,504,693 (Owen, et al.).

In order to prevent premature non-catalytic reaction of the dienes, it is desirable to maintain reactant liquid feedstream temperature below about 180° C. (350° F.) until injection into the fluidized bed. Appropriate thermal insulation or quenching of the feedstream to the injection point can largely prevent gum and coke formation in the liquid phase prior to catalysis.

Figure 2:
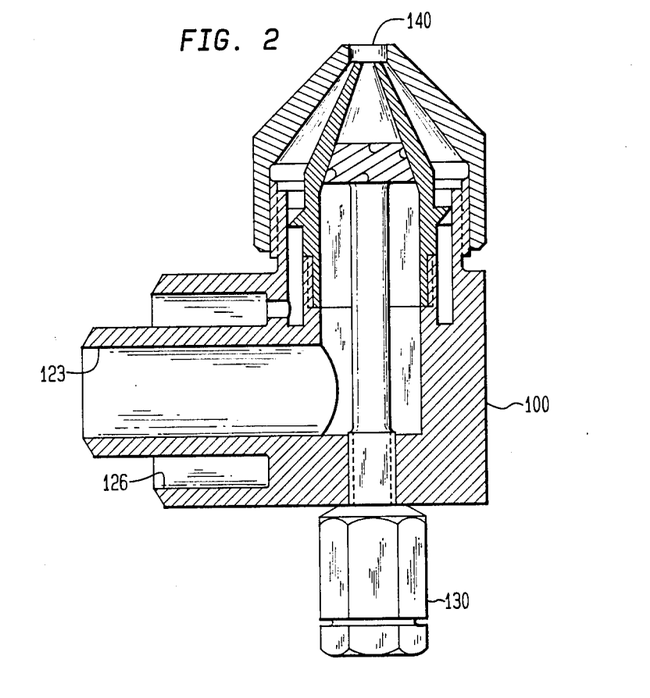
FIG. 2 is a vertical cross section view of a liquid-gas feed nozzle which is employed to introduce low-temperature diene feed into the reactor bed.

Atomization of the pressurized liquid reactant feedstream can be achieved by known techniques, such as liquid spray nozzles, motive gas, ultra sonics, etc. A suitable nozzle is shown in FIG. 2, wherein a concentric feed liquid projection device 100 is depicted in vertical cross section view. Pressurized liquid flows through a supply conduit 123. The nozzle is mounted onto the vessel internal structure by screw cap means 103 or similar attachment means. A motive fluid supplied under pressure through conduit 126 drives the pressurized liquid flowing from the nozzle orifice 140 for injection into the reaction vessel at sufficient velocity to induce a fine vertically directed spray of atomized liquid having an average particle size up to about 300, preferably about 50 microns. The number and arrangement of nozzles will depend upon the cross sectional area of the fluidized bed and fluidization characteristics of the gas-solid-liquid mixture. The atomized stream from a pressurized nozzle can be made to effect penetration into the bed at a depth and/or lateral radius of a meter or more. The mixture fluid may be an inert material, nitrogen, lower aliphatic gas, stream, etc.

Thermal insulation of the liquid diene-containing feedstream from the hot reaction medium in the reaction vessel can be achieved by applying to the liquid feed conduit a layer of thermal insulation, such as a ceramic shield or the like. Jacketed conduits with heat adsorbing fluid may also be suitable.

EXAMPLE 1

In the present example a $C_4^+$ liquid stream is converted to aromatics-rich gasoline in the fluidized bed reactor employing acid ZSM-5 powder catalyst having a fresh alpha value of about 80 at an average conversion temperature about 425° C. (800° F.) and total pressure of about 275 kPa (25 psig). The liquid pyrolysis gasoline feedstock contains about 22 wt. % $C_4^+$ mono-alkenes, 27% $C_4^+$ dienes (mainly 1,3-butadiene), 49% $C_4^+$ paraffins, 2% aromatics and naphthenes, and less than 1% $C_3^-$ aliphatics. Following initial heating and fluidization of the powdered catalyst with a heated lift gas (e.g. $C_2^-$ hydrocarbon), the feedstream is preheated and maintained below 180° C. prior to injection into the bed. After achieving steady state operation at a reaction severity index (R.I.) of about 1, the effluent conversion product (less any lift gas components) comprises 82 wt. % $C_5^+$ liquid gasoline having a research octane rating of 94 (RON). The total aromatics content is 18 wt. %, including 1% benzene (B), 5% toluene (T), 6% xylenes (X) and ethyl benzene, 4% $C_9$ aromatics isomers and 10% $C_{10}$ isomers, mainly durene. The predominant nonaromatic fraction (65%) contains mainly mono-olefins, paraffins and naphthenes, and the light gas $C_4^-$ fraction is 17% of the conversion product.

Typical olefinic pyrolysis byproduct streams are shown in Table 1.

TABLE 1

| Example of Diene-Rich Feestock (ethane cracker byproduct) | |
|---|---|
| Component | Vol. % |
| $C_3^-$ | 1.0 |
| i-butene | 0.08 |
| 1,3-butadiene | 0.51 |
| t.2,butene | 0.1 |
| c.2,butene | 0.15 |
| 1,2 butadiene | 0.14 |
| 3m 1 butene | 0.45 |
| isopentane | 5.44 |
| 1,4 pentadiene | 0.6 |
| 1-pentene | 0.63 |
| n-pentane | 1.92 |
| isoprene | 2.3 |
| c,2,pentene | 0.35 |
| 2m2butene | 0.45 |
| t,1,3, pentadiene | 1.5 |
| c,1,3,pentadiene | 1.0 |
| cyclopentadiene | 13.7 |
| cyclopentene | 1.7 |
| 2,3 d.m. butane | 1.7 |
| 3mpentene | 0.85 |
| hexane | 0.95 |
| unknown $C_6$ | 1.04 |
| cyclohexane | 3.06 |
| benzene | 34.4 |
| unknown $C_8$ | 3.47 |
| Toluene | 10.1 |
| vinyleydohexene | 0.19 |
| ethylbenzene | 1.29 |
| xylene | 1.01 |
| styrene | 0.3 |
| unknown $C_9^+$ | 6.9 |

The above diene-rich stream example contains $C_6^+$ aromatic hydrocarbons which can be separated before feeding to the reactor. Typical ranges of diene-rich pyrolysis gasoline streams comprised of mainly $C_4$–$C_6$ hydrocarbons are:

| | Vol. % |
|---|---|
| Dienes | 5–60 |
| Mono-alkenes | 5–30 |
| Aromatics | 1–5* |
| Alkanes | 20–60 |
| Naphthenes | 1–5 |

*can be as high as 60% if $C_6^+$ fraction is not separated.

EXAMPLES 2-4

A series of continuous olefin conversion runs are conducted using H-ZSM-5 (65%) catalyst having an alpha value of about 175 at the beginning of the aging runs made under oligomerization conditions without regeneration to upgrade mixtures of ethene, propene and butadiene and to determine the effects of diene concentration on catalyst aging. The control feedstock (Example 2) is compared with diene-containing feeds in Table 1.

TABLE 2

|  | Example 2 | Example 3 | Example 4 |
| --- | --- | --- | --- |
| Ethene | 0 | 0.7 | 1.8 |
| Propene | 26.8 | 28.1 | 22.9 |
| Butenes | 35.7 | 31.9 | 31.7 |
| 1,3 Butadiene | 0 (control) | 0.8 | 5.1 |
| Alkanes ($C_4{}^-$) | 37.5 | 38.5 | 38.5 |
| Recycle (mol/mol olefin) | 2.5:1 | 2.5:1 | 2.5:1 |

Figure 3:
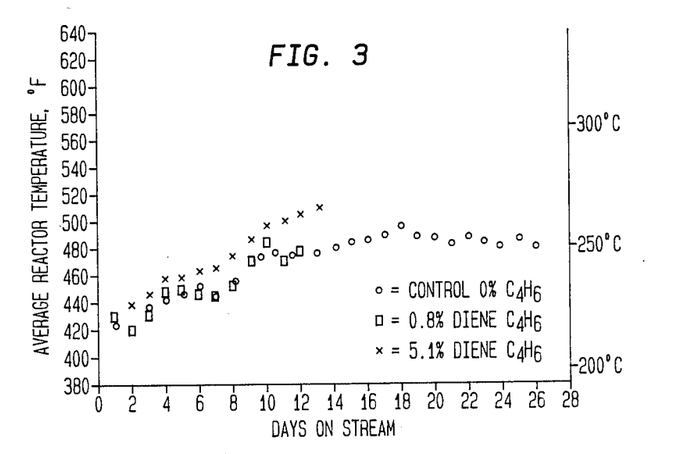
FIG. 3 is an aging plot showing the effect of adding about 1 to 5% of a diene (butadiene) to a $C_2$–$C_4$ olefinic feed.

The conversion unit is a single bed isothermal reactor employing particulate zeolite having a crystal size less than 0.5 microns, together with 35% alumina binder. The continuous runs are conducted at about 6600 kPa and weight hourly space velocity (WHSV) of about 0.8 parts olefin feed per part by weight of catalyst per hour. The conversion runs are started at 205° C. (400° F.) and the temperature is increased to compensate for coke deposition, while maintaining total olefin conversion of at least 80%, preferably over 90%. Results of the aging studies are plotted in FIG. 3, with all conversion rates being normalized to 80% to 330° F.+ product for comparison purposes. Selectivity of the conversion product to heavier hydrocarbons is shown in Table 3.

TABLE 3

|  | Example 2 | Example 3 | Example 4 |
| --- | --- | --- | --- |
| Total Liquid Product, 50% pt, °C. (°F.) | 261/(501) | 259/(498) | 244/(472) |
| Distillate Species (As Cut) |  |  |  |
| 5 wt. %, °C. (°F.) | 232/(434) | 250/(483) | 297(477) |
| 95 wt. % °C. (°F.) | 369/(697) | 383/(722) | 379/(715) |
| Gravity, °API | 44.3 | 41.2 | 38.9 |
| Aniline Point | 177 | 184 | 172 |

While the aromatics product content of the control runs averaged about 2-5%, the 5.1% butadiene feed (Example 4) is upgraded to an aromatics content of 15.5 wt. %, more than 3 times the diene input. The average paraffin content is less than 14% and the liquid dominant product is 70%+olefins and naphthenes.

These results indicate, butadiene, at levels of 1 wt. % or less, do not cause significantly increased catalyst aging or lower product selectivity. Typical FCC $C_3/C_4$ olefins from a depropanizer feed stream contain 0.3-0.6 wt. % butadiene which is less than the 0.8 wt. % butadiene concentration that was used in this study. Even at the 5.1 wt. % butadiene level, though catalyst aging was increased, product selectivity to heavier hydrocarbons remained relatively high.

The flexibility of the fluid bed operating parameters for controlling the reactor temperature under exothermic reaction conditions allows an easy adjustment for achieving the optimal yield structure.

In order to effect fluidization of the catalyst at the bottom of the reactor prior to injection of the liquid feed stream, a lift gas may be employed. This can be an inert diluent or recycled light gas, such as methane, ethane, ethene, propane, etc. Recycle of $C_3{}^-$ light hydrocarbons may also be desirable under certain circumstances, for instance with unreacted aliphatics which requiure further conversion or for dilution of highly exothermic feedstocks.

The thermodynamic balance of exothermic olefin oligomerization and endothermic paraffin reactions can have significant impact on the reaction severity conditions.

The use of a fluid-bed reactor in this process offers several advantages over a fixed-bed reactor. Due to continuous catalyst regeneration, fluid-bed reactor operation will not be adversely affected by oxygenate, sulfur and/or nitrogen containing contaminatants present in the pyrolysis byproduct.

While the invention has be shown by describing preferred embodiments of the process, there is no intent to limit the inventive concept, except as set forth in the following claims.

We claim:

1. A continuous system for catalytic conversion of diolefin-rich hydrocarbon feedstock to heavier hydrocarbons under essentially isothermal conditions is elevated temperature, comprising in combination:

enclosed vertical reactor means without baffles containing a fluidized bed of solid conversion catalyst particles in turbulent flow regime;

heat exchange means in said reactor for controlling reaction zone temperature;

particle separator means contained within said reactor for separation of catalyst particles and product effluent;

bottom inlet means for receiving a fluidizing hydrocarbon vapor stream and passing the hydrocarbon vapor stream upwardly through the catalyst bed to maintain turbulent fluidized bed catalyst flow;

grid means for distributing said fluidizing hydrocarbon vapor stream above said bottom inlet means;

liquid pump means for pressure injecting an atomized stream of cold liquid feedstock deep into the reaction zone;

thermally insulated conduit means connected to said liquid pump for transporting said stream of liquid feedstock into said reaction zone above said grid means at a temperature below reaction zone temperature;

thermally insulated atomizing nozzle means for atomizing said stream of liquid feedstock connected to said conduit means to provide an atomized feedstock stream with an average particle size not greater than 300 microns;

catalyst regenerator means operatively connected to said vertical reactor means for regenerating spent catalyst particles for recycle to said reactor.

2. The continuous system of claim 1 wherein said solid catalyst particles comprise medium pore pentasil zeolite having an apparent alpha value of about 10 to 250, an average particle size of about 20 to 100 microns, including at least 10 weight percent fine particles having a particle size less then 32 microns.

3. The reactor system of claim 1 wherein said atomizing nozzle comprises:

thermally insulated convergent nozzle housing;

orifice means for injecting said liquid feedstream into a reaction zone, connected to said housing at a locus of maximum convergence;

first conduit means, within said housing and in communication with said orifice means, for transferring said feedstream thereto;

second conduit means within said housing concentrically disposed about said first conduit and in communication with said orifice means, for transferring cold pressurized atomizing motive fluid thereto, whereby atomized liquid feedstream particles are injected into a reaction zone;

attachment means connected to said nozzle housing for connecting said nozzle to a reaction vessel.

* * * * *

UNITED STATES PATENT AND TRADEMARK OFFICE
CERTIFICATE OF CORRECTION

PATENT NO. : 4,778,661

DATED : October 18, 1988

INVENTOR(S) : Amos A. Avidan, Fritz A. Smith and Samuel A. Tabak

It is certified that error appears in the above-identified patent and that said Letters Patent is hereby corrected as shown below:

Abstract, line 19, "efluent" should be --effluent--
Column 1, line 21, "enironmentally" should be --environmentally--
Column 1, line 56, "dislcosed" should be --disclosed--
Column 2, line 45, "rapdily" should be --rapidly--
Column 3, line 33, "zoelitic" should be --zeolitic--
Column 3, line 51, "tp" should be --to--
Column 4, line 44, "feestock" should be feedstock--
Column 4, line 47, "otherise" should be --otherwise--
Column 5, line 27, "hydrocarbonds" should be --hydrocarbons--
Column 5, line 30, "peferrable" should be --preferable--
Column 5, line 60, "gasoues" should be --gaseous--
Column 9, line 20, "atmostpheric" should be --atmospheric--
Column 12, line 3, "requiure" should be --require--
Column 12, line 14, "contaminatants" should be --contaminants--

UNITED STATES PATENT AND TRADEMARK OFFICE
CERTIFICATE OF CORRECTION

PATENT NO. : 4,778,661

DATED : October 18, 1988

INVENTOR(S) : Amos A. Avidan et al.

It is certified that error appears in the above-identified patent and that said Letters Patent is hereby corrected as shown below:

Column 12, claim 1, line 23, "is" should be -- at --.

Signed and Sealed this

Twenty-eighth Day of March, 1989

Attest:

DONALD J. QUIGG

*Attesting Officer*   *Commissioner of Patents and Trademarks*